US005356614A

United States Patent [19]

Sharma

[11] Patent Number: 5,356,614
[45] Date of Patent: Oct. 18, 1994

[54] PROCESS OF PREPARING MICROPARTICULATE COLLAGEN COLLAGEN-BASED PRODUCTS PRODUCED THEREBY AND METHOD OF APPLYING SAME

[75] Inventor: Vinay K. Sharma, Long Valley, N.J.

[73] Assignee: Mixro-Collagen Pharmaceutics, Ltd., Brick, N.J.

[21] Appl. No.: 985,802

[22] Filed: Dec. 2, 1992

Related U.S. Application Data

[60] Continuation-in-part of Ser. No. 835,557, Feb. 14, 1992, which is a division of Ser. No. 405,520, Sep. 11, 1989.

[51] Int. Cl.[5] .............................................. A61L 15/00

[52] U.S. Cl. ..................................... 424/45; 424/485; 424/488; 424/499

[58] Field of Search ................. 424/45, 487, 445, 499, 424/488; 514/963

[56] References Cited

U.S. PATENT DOCUMENTS

| | | | |
|---|---|---|---|
| 4,741,872 | 5/1988 | DeLuca et al. | 514/963 |
| 4,950,699 | 8/1990 | Holman | 424/445 |
| 5,059,425 | 10/1991 | Tsiliary et al. | 424/445 |
| 5,128,136 | 7/1992 | Bentley et al. | 424/445 |

*Primary Examiner*—Thurman K. Page
*Assistant Examiner*—William E. Benston, Jr.
*Attorney, Agent, or Firm*—Louis E. Marn

[57] ABSTRACT

There is disclosed a collagen preparation of improved adhesive properties and formed of microparticulate collagen of a particle size of from 0.5 to 2 μm, preferably 0.5 to 1.0 μm preferably submicrosized in a delivery system, such as an aerosol, and thus in sprayable form as a wound dressing alone, or with releasing drugs or other active agents. The microparticulate collagen is formed by ball milling collagen for a time sufficient to form the microparticulate collagen having a particle size of from 0.5 to 2 μm, preferably 0.5 to 1 μm.

7 Claims, No Drawings

PROCESS OF PREPARING MICROPARTICULATE COLLAGEN COLLAGEN-BASED PRODUCTS PRODUCED THEREBY AND METHOD OF APPLYING SAME

RELATED APPLICATIONS

The application is a continuation-in-part of application U.S. Ser. No. 07/835,557, filed Feb. 14, 1992 which is a divisional application of U.S. Ser. No. 07/405,520, filed Sep. 11, 1989.

BACKGROUND OF THE INVENTION

1. Field of the Invention

This invention relates to drug delivery systems, and more particularly to epidermal/dermal, tissue adhesive, microcollagen, collagen-based drug delivery systems and process for producing same.

2. Description of the Prior Art

In the copending application, there is disclosed a process for ball milling collagen to a particle size of from about 1 to 50 μm, preferably 5 to 25 μm for incorporation into a drug delivery system, such as an aerosol application as a wound dressing. Such particulate collagen, as particularly included for aerosol application, has been found to be effective; however, some of the particulate collagen did not appear to adequately adhere to the wound site or was readily removed therefrom by the slightess contact thereby reducing effectiveness of collagen deposition.

OBJECTS OF THE PRESENT INVENTION

An object of the present invention is to provide an improved process for particulating collagen to a size exhibiting more effective adhesion.

Another object of the present invention is to provide improved particulate collagen capable of non-aerosol application, such as paste and gel dosage forms.

Yet another object of the present invention is to provide improved particulate collagen of improved adhesion properties to the wound surface for effective healing.

Still another object of the present invention is to produce an adhesive film treatment for minor skin irritations.

A still further object of the present invention is to produce particulate collagen of improved suspendability in aerosol propellants and thereby to enhance uniformity in the delivery dosages.

A further object of the present invention is to provide improved particulate collagen for prolonged and complete coverage to urine and stool-related scalds which require frequent regimens of application of standard dosage forms, such as barrier creams and sprays which are washed away or flaked off due to incontinence or patient movement.

A further object of the present invention is to produce an adhesive wound healing film barrier that does not require additional protection by gauze or wet-to-dry gauze dressing for keeping particulate collagen in place.

A further object of the present invention is to apply films of particulate collagen in successive applications before cultured skin graft to increase the chance of "take" of the "artificial skin" or the skin graft.

A further object of the present invention is to produce an adhesive particulate adhesive collagen film that seals the periphery of "artificial skins" designed to treat skin loss due to pressure sores or second to third degree burns.

A further object of the present invention is to produce a sprayable particulate adhesive collagen film consistent and biocompatible with collagen-based artificial skins.

SUMMARY OF THE INVENTION

These and other objects of the present invention are achieved by ball milling collagen into particulate collagen of a particle size of from 0.1 to 5.0 μm, preferably 0.5 to 2 μm, and the inclusion of such particulate collagen in delivery systems, such as an aerosol, paste, and gel, and with releasing drugs or other active agents. The particulate collagen comprises up to about 10% by weight of the resulting delivery system in case of aerosol and about 25% by weight of the paste or gel.

DETAILED DESCRIPTION OF THE INVENTION

Collagen employed for preparation into an aerosol form for wound treatment and an adjunct treatment to grafting of "artificial skin", as well as other forms, such as paste and gel for drug delivery is derived from native collagen free of foreign materials and completely resorbable by the user's body. Such collagen is in the form of insoluble material having a molecular weight in excess of 285,000. For the purposes of the present invention, the collagen powder is in the form of discrete particles having a particle size range of from about 0.1 to 5.0 μm preferably 0.5 to 2 μm, more of sub micron dimensions. Said particulate collagen absorbs 10 to 50 times its weight of water and expands 3 to 5 times in volume.

The particuate collagen of the present invention is suitably prepared by milling an appropriate collagen in a Ball Mill in an inert media, such as alcohol or water under processing conditions of about 60% charge at 50 revolutions per minute for 60 to 96 hours, preferably at least about 72 hours. Native, purified collagen fibers are mixed with a low molecular weight alcohol, such as isopropyl or denatured alcohol, at a collagen to liquid ratio of 1:25 to 1:100, preferably 1:50 to form a collagen dispersion of up to 2% w/v. The collagen dispersion may be mixed with different GRAS (generally recognized as safe) materials, such as calcium alginate for controlling bleeding, absorbing wound exudate, and filling deep decubitus ulcers and with zinc oxide to accelerate the overall kinetics of wound healing and of pharmacological agents, such as antibiotics for prevention of infection, silver sulfadiazine for preventing wound sepsis in patients with second and third degree burns, antifungal agents for managing itching associated with Athlete's foot or Jock itch, and finally growth factors, such as platelet-derived growth factor, epidermal growth factor, transforming growth factor beta, and anglogenesis factor for accelerating wound healing. The resulting collagen-adjuvant-alcohol dispersion is sealed into an aerosol can and the can is pressurized by dispensing propellants to the can whereby the aerosol can delivers collagen-based formulations to the cutaneous substrate at the rate of about 6 g per 10 seconds while maintaining the can pressure at about 60 psig.

EXAMPLES OF THE INVENTION

The specific nature of the composition of the present invention will be more fully apparent from considerations of the following specific examples of preferred embodiments thereof.

EXAMPLE 1

20.0 g. sample of purified collagen Type I is added to a Ball Mill with the subsequent addition of 2.0 L of isopropyl alcohol. Milling is effected for 96 hours to prepare a smooth dispersion of collagen powder of a particle size of from 0.1 to 2.0 μm. The 2% w/v dispersion is centrifuged to obtain a 10% w/w dispersion of purified collagen Type I.

EXAMPLE II 8.5 g of the collagen dispersion of Example 1 is introduced into a 6 ounce rated aerosol can and a valve assembly crimped into the can. The valve assembly is comprised of 2×20/1000 stem with a 20/1000 stainless steel spring. The valve body is 62/1000 in dimensions with a 30/1000 with a vapor tap conical cup, epon-coated. The internal diameter of the dip tube is 50/1000. 76.5 g of a 65/35 blend of difluoroethane and isobutane is added to the rated aerosol can. A 25/1000 Standard Taper (ST) actuator (Precision Valve Company) is inserted into the valve assembly. The actuator is pushed to generate a white spray of a collagen-based material which upon evaporation deposits itself as a translucent film on the substrate.

EXAMPLE III 90.0 g of the 10% w/w collagen dispersion of Example 1 (milling time 72 hours) is added to a Ball Mill with the addition of 10.0 g of calcium alginate (Kelco International Limited). Milling is effected for 24 hours to produce a dispersion of collagen powder of a particle size from 0.1 to 2.0 μm and calcium alginate powder of a particle size of from 1 to 5 μm.

EXAMPLE IV 8.5 g. of the collagen dispersion of Example III is introduced into a 6 ounce tared aerosol can and a valve assembly crimped into the can. The valve assembly is comprised of 2×20/1000 stem with a 20/1000 stainless steel spring. The valve body is 62/1000 in dimensions with a 30/1000 with a vapor tap conical cup, epon-coated. The internal diameter of the dip tube is 50/1000. 76.5 g of a 65/35 blend of Propellant 152a and Propellant A-31 is added to the rated aerosol can. A 25/1000 Standard Taper (ST) actuator (Precision Valve Company) is inserted into the valve assembly. The actuator is pushed to generate a white spray of a collagen-based material which upon evaporation deposits itself as a translucent film on the substrate.

EXAMPLE V 92.0 g of the 10% w/w collagen dispersion of Example I (milling time 72 hours) is added to a Ball Mill with the addition of 8.0 g of zinc oxide (Mallinckrodt, Inc., St. Louis). Milling is effected for 24 hours to produce a dispersion of collagen powder of a particle size from 0.1 to 2.0 μm and zinc oxide powder of a particle size of from 1 to 5 μm.

EXAMPLE VI 8.5 g of the collagen dispersion of Example V is introduced into a 6 ounce rated aerosol can and a valve assembly crimpted into the can. The valve assembly is comprised of 2×20/1000 stem with a 20/1000 stainless steel spring. The valve body is 62/1000 in dimensions with a 30/1000 with a vapor tap conical cup, epon-coated. The internal diameter of the dip tube is 50/1000. 76.5 g of a 65/35 blend of Propellant 152a and Propellant A-31 is added to the rated aerosol can. A 25/1000 Standard Taper (ST) actuator (Precision Valve Company) is inserted into the valve assembly. The actuator is pushed to generate a white spray of a collagen-based material which upon evaporation deposits itself as a translucent film on the substrate.

EXAMPLE VII 99.0 g of the 10% w/w collagen dispersion of Example 1 (milling time 72 hours) is added to a Ball Mill with the addition of 1.0 g of silver sulfadiazine (Napp Chemicals, Inc.). Milling is effected for 24 hours to produce a dispersion of collagen powder of a particle size from 0.1 to 2.0 μm and silver sulfadiazine powder of a particle size of from 1 to 5 μm.

EXAMPLE VIII 8.5 g of the collagen dispersion of Example VII is introduced into a 6 ounce rated aerosol can and a valve assembly crimped into the can. The valve assembly is comprised of 2×20/1000 stem with a 20/1000 stainless steel spring. The valve body is 62/1000 in dimensions with a 30/1000 with a vapor tap conical cup, epon-coated. The internal diameter of the dip tube is 50/1000. 76.5 g of a 65/35 blend of Propellant 152a and Propellant A-31 is added to the rated aerosol can. A 25/1000 Standard Taper (ST) actuator (Precision Valve Company) is inserted into the valve assembly. The actuator is pushed to generate a white spray of a collagen-based material which upon evaporation deposits itself as a translucent film on the substrate.

EXAMPLE IX 20.0 g sample of purified collagen Type I is added to a Ball Mill with the subsequent addition of 2.0 L of purified water. Milling is effected for 96 hours to prepare a smooth dispersion of collagen powder of a particle size of from 0.1 to 2.0 μm. The 2% w/v dispersion is centrifuged to obtain a 25% w/w aqueous paste of purified collagen Type I.

EXAMPLE X 30.0 g of the 25% w/w aqueous paste is added to an aluminum tube, crimped and capped. The product is sterilized by gamma irradiation at 2.5 megarad.

Another advantage of the present invention is the incorporation into and the subsequent delivery from the microparticulate collagen of pharmacological agents such as platelet-derived growth factor, epidermal growth factor, transforming growth factor, beta angeogenesis factor, antihistamines, analgesics, anti-inflammatory agents, antibiotics, antifungal agents, spermicidal agents, hormones, enzymes, or enzyme inhibitors.

While the invention has been described in connection with an exemplary embodiment thereof, it will be understood that many modifications will be apparent to those of ordinary skill in the art, and that this application is intended to cover any adaptations or variations thereof. Therefore, it is manifestly intended that this invention be only limited by the claims and the equivalents thereof.

What is claimed is:

1. A process for particulating collagen, which comprises:

a) introducing collagen with an inert media into a ball mixing zone;

b) ball milling for a time sufficient to form microparticulate collagen having a particle size of from 0.1 to 5.0 μm; and c) recovering said microparticulate collagen.

2. The process as defined in claim 1 wherein ball milling is effected for a time sufficient to produce submicroparticulate collagen of a particle size of from 0.5 to 2.0 μm.

3. The process as defined in claim 1 wherein said inert media is a low molecular weight alcohol.

4. The process as defined in claim 2 wherein collagen to inert liquid is in a ratio of from 1:5 to 1:50.

5. The process as defined in claim 3 wherein said ratio is preferably 1:10 to 1:15.

6. The process as defined in claim 1 wherein ball milling is effected for from 60 to 90 hours.

7. The process as defined in claim 6 wherein ball milling is effected for about 72 hours.

* * * * *